United States Patent
Bussa et al.

(10) Patent No.: US 9,237,862 B2
(45) Date of Patent: Jan. 19, 2016

(54) DIAGNOSIS OF ASTHMA

(75) Inventors: Nagaraju Bussa, Bangalore (IN); Kumar Thirunellai Rajamani, Bangalore (IN); Abhishek Jain, Bangalore (IN)

(73) Assignee: KONINKLIJLE PHILIPS N.V., Eindhoven (NL)

( * ) Notice: Subject to any disclaimer, the term of this patent is extended or adjusted under 35 U.S.C. 154(b) by 597 days.

(21) Appl. No.: 13/203,838

(22) PCT Filed: Mar. 4, 2010

(86) PCT No.: PCT/IB2010/050933
§ 371 (c)(1),
(2), (4) Date: Dec. 13, 2011

(87) PCT Pub. No.: WO2010/103435
PCT Pub. Date: Sep. 16, 2010

(65) Prior Publication Data
US 2012/0089042 A1    Apr. 12, 2012

(30) Foreign Application Priority Data

Mar. 10, 2009 (EP) ..................... 09154707

(51) Int. Cl.
*A61B 5/113* (2006.01)
*A61B 5/00* (2006.01)

(52) U.S. Cl.
CPC .............. *A61B 5/113* (2013.01); *A61B 5/6819* (2013.01); *A61B 5/6822* (2013.01); *A61B 5/6833* (2013.01); *A61B 2562/0261* (2013.01)

(58) Field of Classification Search
CPC .......... A61B 5/08; A61B 5/11; A61B 5/1107; A61B 5/113; A61B 5/6819; A61B 5/6822
USPC ................................................... 600/529–534
See application file for complete search history.

(56) References Cited

U.S. PATENT DOCUMENTS 5,178,151 A * 1/1993 Sackner .................... 600/485
5,423,328 A   6/1995 Gavish
(Continued)

FOREIGN PATENT DOCUMENTS

CN       2525941 Y    12/2002
JP    2007525236 A     9/2007
(Continued)

OTHER PUBLICATIONS

Kesten et al. "Respiratory Rate during Acute Asthma." Chest. Jan. 1990;97(1):58-62.*

(Continued)

*Primary Examiner* — Navin Natnithithadha
*Assistant Examiner* — Meredith Weare
(74) *Attorney, Agent, or Firm* — Michael W. Haas

(57) ABSTRACT

An apparatus (200) for diagnosing asthma is disclosed. The apparatus (200) comprises a data acquisition module (210) configured to acquire at least one physical deformation feature associated with at least one of nasal flaring, neck retraction and inter-coastal retraction of a subject under examination and an analysis module (220) configured to analyze the acquired at least one physical deformation feature associated with at least one of the nasal flaring, the neck retraction and the inter-coastal retraction of the subject under examination and diagnose the asthma based on the analyzed at least one physical deformation feature associated with at least one of the nasal flaring, the neck retraction and the inter-coastal retraction of the subject under examination. The disclosed apparatus (200) can be used for monitoring asthma at home, at hospital or in ambulatory patients.

10 Claims, 8 Drawing Sheets

(56) References Cited

U.S. PATENT DOCUMENTS

| | | | |
|---|---|---|---|
| 6,283,923 B1 * | 9/2001 | Finkelstein et al. | 600/532 |
| 7,077,810 B2 | 7/2006 | Lang et al. | |
| 7,902,373 B2 * | 3/2011 | Blake et al. | 546/300 |
| 2003/0100843 A1 * | 5/2003 | Hoffman | 600/538 |
| 2004/0077934 A1 | 4/2004 | Massad | |
| 2005/0119586 A1 | 6/2005 | Coyle | |
| 2005/0131288 A1 * | 6/2005 | Turner et al. | 600/391 |
| 2007/0197882 A1 * | 8/2007 | Smith et al. | 600/300 |
| 2008/0146569 A1 * | 6/2008 | Blake et al. | 514/235.5 |
| 2008/0262370 A1 * | 10/2008 | Varney et al. | 600/532 |
| 2008/0269625 A1 | 10/2008 | Halperin et al. | |
| 2009/0259135 A1 * | 10/2009 | Stasz | 600/534 |
| 2010/0286546 A1 * | 11/2010 | Tobola et al. | 600/534 |

FOREIGN PATENT DOCUMENTS

| | | |
|---|---|---|
| JP | 2009501557 A | 1/2009 |
| WO | WO9011042 A1 | 10/1990 |
| WO | W02006137067 A2 | 12/2006 |

OTHER PUBLICATIONS

Cham, GW et al: "Clinical Predictors of Acute Respiratory Acidosis During Exacerbation of Asthma and Chronic Obstructive Pulmonary Disease", EP Journal Emergence Medicine, Chapman and Hall, London, GB, Sep. 1, 2002, vol. 9, No. 3, pp. 225-232.

* cited by examiner

DIAGNOSIS OF ASTHMA

FIELD OF THE INVENTION

The subject matter relates to diagnosis of asthma.

BACKGROUND OF THE INVENTION

U.S. Pat. No. 7,077,810 discloses a method for predicting an onset of clinical episode, the method including sensing breathing of a subject, determining at least one breathing pattern of the subject responsively to the sensed breathing, comparing the breathing pattern with a baseline breathing pattern and predicting the onset of the clinical episode at least in part responsively to the comparison. Predicting the onset of the clinical episode may not be reliable and there could be variations in diagnosing asthma.

SUMMARY OF THE INVENTION

It is an object of the present subject matter to improve the diagnosis of asthma.

The object of the present subject matter is realized by providing an apparatus for diagnosing asthma, the apparatus comprising a data acquisition module configured to acquire at least one physical deformation feature associated with at least one of nasal flaring, neck retraction and intercostal retraction of a subject under examination; and an analysis module configured to analyze the acquired at least one physical deformation feature associated with at least one of the nasal flaring, the neck retraction and the intercostal retraction of the subject under examination and diagnose the asthma based on the analyzed at least one physical deformation feature associated with at least one of the nasal flaring, the neck retraction and the intercostal retraction of the subject under examination.

Generally, as breathing becomes more difficult, areas of the chest where retractions can be seen increases. It has been observed that a) mild difficulty in breathing can cause retraction in the abdomen, just below the rib cage (sub coastal) and at the bottom of the breastbone (sub sternal)

b) moderate difficulty in breathing can cause retraction in the same areas of the chest and abdomen as in mild difficulty in breathing and between the ribs (intercostal)

c) severe difficulty in breathing can cause retraction in the same areas of the chest and abdomen as mild and moderate difficulty in breathing and in the neck, just above the collarbone (supra clavicular) or just above the breastbone (supra sternal).

Generally, symptoms of asthma include i) nasal flaring wherein nostril size increases with breathing ii) neck retraction wherein neck area moves inward with breathing and iii) intercostal retraction wherein skin between or below the ribs move inward with breathing.

Nasal flaring, chest retraction and neck retraction signifies dysfunctional breathing pattern and is a characteristic of airway obstruction particularly asthma. The physical deformations caused on the nose, the intercostal spaces and the neck are the locations where distressed breathing generally gets manifested. Hence, monitoring and analyzing these physical deformations can enable an objective evaluation of the severity of the underlying obstructive respiratory disease. This can improve the diagnosis and management of asthma.

The disclosed apparatus can provide valuable input to arrive at the diagnosis of the possible asthmatic attack since the nasal flaring, the neck retraction and the intercostal retraction would occur during the episode of the asthma.

The diagnosis based on the physical deformations of the nose, the neck and the chest can be accurate and more reliable. The diagnosis is non-invasive and simple. Further, the asthma can be diagnosed at incipient stage and can obviate the development and precipitation of the full blown attack.

In an embodiment of the apparatus, the data acquisition module comprises at least one strain gauge configured to acquire at least one physical deformation feature associated with at least one of the nasal flaring, the neck retraction and the intercostal retraction of the subject under examination during at least one respiratory cycle, the at least one physical deformation feature being acquired in the form of electrical variation associated with at least one of the nasal flaring, the neck retraction and the intercostal retraction of the subject under examination.

The strain gauge can be attached to the nostrils or to the neck or to the intercostal region with the help of a suitable adhesive such as cyano-acrylate. The disclosed apparatus can facilitate the placement of the at least one strain gauge a) below or atop the tip of the nostril for acquiring at least one physical deformation feature associated with the nasal flaring b) in the area of the neck either bilaterally on right and left sides or unilaterally in between the lateral border of the sternocleidomastoid muscle and the upper border of the clavicle bone for acquiring at least one physical deformation feature associated with the neck retraction c) in one or more of the nine intercostal spaces in front of the chest either unilaterally or bilaterally for acquiring at least one physical deformation feature associated with the intercostal retraction The strain gauge can help in the measurement of physical deformations that evolve over time in the form of nasal flaring and suction of skin over the intercostal spaces and the neck region. As the nostrils or the neck region or the intercostal region deforms, the foil is also deformed, causing its electrical resistance to change. This resistance change can be measured using a Wheatstone bridge, which is related to the strain by a quantity known as gauge factor.

The idea disclosed is to measure the strain generated due to nasal flaring, chest and neck retraction and diagnose asthma based on the measurements.

In some embodiments, the at least one strain gauge is a mercury-in-rubber strain gauge. This kind of strain gauge consists of a small amount of liquid mercury enclosed in a small rubber tube, which is applied around the body part (nostrils, neck region and intercostal region). Physical deformation of the body part (nostrils, neck region and intercostal region) results in stretching of the tube, making it both longer and thinner, which increases electrical resistance. The advantages of using strain gauge are i) there are no moving parts ii) relatively simple in construction iii) small in size and iv) easy to dispose within the disclosed apparatus.

In a still further embodiment, the apparatus comprises a recording module configured to digitally record for a pre-determined time period the acquired at least one physical deformation feature in the form of electrical variation associated with at least one of the nasal flaring, the neck retraction and the intercostal retraction of the subject under examination;

a feature extraction module configured to extract time domain feature and/or frequency domain feature from the digitally recorded at least one physical deformation feature in the form of electrical variation associated with at least one of the nasal flaring, the neck retraction and the intercostal retraction of the subject under examination; and a storing module configured to store the extracted time domain feature and/or frequency domain feature electrical variation associated with at least one of the nasal flaring, the neck retraction and the intercostal retraction of the subject under examination.

This embodiment is well suited for home use. The parents can use the disclosed apparatus for recording and storing the extracted physical deformation features of their child associated with the neck retraction, the nasal flaring and the intercostal retraction. During the scheduled visit to the hospital, the doctor can analyze and interpret the stored recordings and diagnose the condition of the child for asthma.

Recording and storing the extracted features can a) help the doctor to flawlessly formulate the clinical profile of the child (patient or subject) and prescribe suitable treatment b) be useful for effective monitoring of the subjects already under treatment especially small children known to have asthma to have precise understanding of symptom evolution and remission c) act as a history for tracking the trend of disease evolution d) be clinically useful for especially young children, infants and elderly patients, patients with mental retardation or other behavioral disorders since these are the group of subjects (patients or children) who may not be able to conceive and convey their breathing problems accurately to the doctor.

Further, by the time the subject (patient or child) reaches the doctor the disease symptoms and signs would have subsided at least partially. This can give an incomplete clinical picture to the doctor. This can result in incorrect diagnosis. The stored extracted physical deformation features associated with at least one of the nasal flaring, the neck retraction and the intercostal retraction can overcome the risk of making incorrect diagnosis. This embodiment finds its use amongst both the subjects (patients or child) and the doctor in home scenarios.

In a still further embodiment, the feature extraction module is configured to extract at least one of a) the respiratory cycles associated with at least one of the nasal flaring, the neck retraction and the intercostal retraction b) the average of the electrical variations over a pre-determined number of respiratory cycles associated with at least one of the nasal flaring, the neck retraction and the intercostal retraction c) the frequency bands present in the respiratory cycles associated with at least one of the nasal flaring, the neck retraction and the intercostal retraction d) the minimum frequency band and the maximum frequency band present in the respiratory cycles associated with at least one of the nasal flaring, the neck retraction and the intercostal retraction.

The symptoms of asthma can be better understood with the help of the extracted features. This can also help in carrying out a comparative analysis with other available baseline features and can further improve the diagnosis of asthma.

In a still further embodiment, the analysis module further comprises an input module configured to receive input, the input being at least one of gender, age, height, weight and ethnicity of the subject under examination; and a pre-classified calibrated database having data associated with non-asthmatic subjects and asthmatic subjects, the data being at least one of i) gender
ii) age
iii) height
iv) weight
v) ethnicity
vi) time domain and/or frequency domain features extracted using the acquired physical deformations in the form of electrical variation associated with at least one of the nasal flaring, the neck retraction and the intercostal retraction
vii) condition of the subject: non-asthmatic, onset of asthma, mild asthma, acute asthma The input module helps to collect data of the subject under examination. This input data can help in grouping the subjects and identifying symptoms related to asthma within the groups. Further, the collected data can help in carrying out a comparative study of the extracted physical deformation features with similar subjects. This can further improve the diagnosis of asthma.

Further, in developing countries, where economies do not permit every family to own the disclosed apparatus, families can own a shared apparatus which can be used on a need basis. In such cases, the input module can be of help to identify the subject under examination and the stored physical deformation features associated with at least one of the nasal flaring, the neck retraction and the intercostal retraction of the subject under examination.

The pre-classified calibrated database can act as a baseline. It can help in analyzing and classifying the physical deformations of the subject under examination associated with at least one of the nasal flaring, the intercostal retraction and the neck retraction into different grades of asthma. The different grades of asthma can be onset of asthma, mild asthma and severe asthma.

The pre-classified calibrated database can be periodically updated. This can be done by testing the disclosed apparatus across sufficient number of subjects based on age, height, weight, gender and ethnicity. The physical deformations associated with at least one of the nasal flaring, the neck retraction, and the intercostal retraction can be acquired. The time domain and/or frequency domain features can be extracted, labeled as non-asthmatic/asthmatic subject and stored. The pre-classified calibrated database can further aid in improving the diagnosis of asthma.

In a still further embodiment, the analysis module comprises a logic module configured to compare the extracted time domain and/or frequency domain physical deformations associated with at least one of the nasal flaring, the neck retraction and the intercostal retraction of the subject under examination with the data available in the pre-classified calibrated database and diagnose the asthma condition of the subject under examination and store the diagnosis related information.

Known pattern matching algorithms can be used to compare the extracted physical deformation time domain and/or frequency domain features associated with at least one of the nasal flaring, the neck retraction and the intercostal retraction with the extracted physical deformation time domain and/or frequency features available in the pre-classified calibrated database. The condition of the subject under examination can be obtained based on pattern matching results. It is also possible to obtain the grade of the asthma e.g. onset of asthma, mild asthma or severe asthma.

In some embodiments, a Support Vector Machine (SVM) can be used for classification. As an illustrative example, the SVM can view input data as two sets of vectors; one set corresponding to the actual features extracted using the strain gauges and the other set corresponding to the data available in the pre-classified calibrated database of asthmatic and non-asthmatic subjects. The SVM can construct a separating hyper plane in an n-dimensional space, the hyper plane being the one which maximizes the margin between the two data sets. To calculate the margin, two parallel hyper planes can be constructed, one on each side of the separating hyper plane, which is "pushed up against" the two data sets. Intuitively, a good separation can be achieved by the hyper plane that has the largest distance to the neighboring data points of both classes, since in general the larger the margin the better the generalization error of the classifier.

In a still further embodiment, the apparatus comprises a notification module, the notification module being at least one of a visual display unit, an audio unit or a colored light generation unit, the notification module configured to notify i) whether at least one of the nasal flaring, the neck retraction and the intercostal retraction is detected ii) the need for emergency consultation if the diagnosed asthma is above a pre-determined threshold iii) that there is no need for emergency consultation if the diagnosed asthma is below a pre-determined threshold.

This embodiment has the following advantages i) it can avoid panic and discomfort of having severe asthmatic attack ii) minimize the need for emergency visits or hospitalizations iii) can bring down the cost of treatment by avoiding unnecessary consultation iv) can prevent recurrent exacerbations of asthma.

The disclosed apparatus can notify the results in the form of visual display and indicate the severity of asthma to the subject under examination. Alternately, an alarm beep could guide both the adult patients and the anxious parents of the sick children to seek medical consultation immediately in case of severe asthma.

The disclosed apparatus can also give information directly in the form of colored lights as to whether the nasal flaring, the neck retraction and the intercostal retraction are present. Further, the waveforms representing the physical deformations associated with at least one of the nasal flaring, the neck retraction and the intercostal retraction can be displayed. This can form reliable input to the doctor to objectively evaluate the symptoms thereby easing the normal work flow of asthma diagnosis, assessment of asthma severity and response to treatment. This can further improve the diagnosis and management of asthma.

The subjective evaluation of nasal flaring, intercostal retraction and neck retraction may not be reliable. There could be some variations in inter-observer (i.e. between different doctors) agreement on intercostal retractions and interpretation. To overcome these limitations, the nasal flaring, the neck retractions and the intercostal retractions are recorded and the extracted features are stored in digital form. The stored features can be visualized by the doctor. This can further aid in improving the diagnosis of asthma by providing objective information about the symptoms.

In a still further embodiment, the apparatus further comprises an evaluation module configured to evaluate the progress of the therapy or remission based on i) the currently acquired at least one physical deformation feature associated with at least one of the nasal flaring, the neck retraction and the intercostal retraction of the subject under examination ii) the previously stored physical deformation feature associated with at least one of the nasal flaring, the neck retraction and the intercostal retraction of the subject under examination.

The disclosed apparatus can be used to assess the evolution of asthma and the response to treatment as it provides objective measurements of asthma severity in the form of reduction/increase in the nasal flaring, the chest retraction and the intercostal retraction during the period of remission.

In some embodiments, the data from the strain gauges can be fed wirelessly or through wired connection to a wheeze monitoring device. The wheeze monitoring device can subsequently use this data as an additional input along with the wheezes to estimate the severity of asthma. This can further improve the diagnosis of asthma.

The object of the present subject matter is further realized by providing a method for diagnosing asthma, the method comprising:

acquiring at least one physical deformation feature associated with at least one of nasal flaring, neck retraction and intercostal retraction; and analyzing the acquired at least one physical deformation feature associated with at least one of the nasal flaring, the neck retraction and the intercostal retraction and diagnosing asthma based on the analyzed at least one physical deformation feature associated with at least one of the nasal flaring, the neck retraction and the intercostal retraction.

BRIEF DESCRIPTION OF THE DRAWINGS

The above-mentioned aspects, features and advantages will be further described, by way of example only, with reference to the accompanying drawings, in which the same reference numerals indicate identical or similar parts, and in which.

DETAILED DESCRIPTION OF THE EMBODIMENTS

Figure 1A:
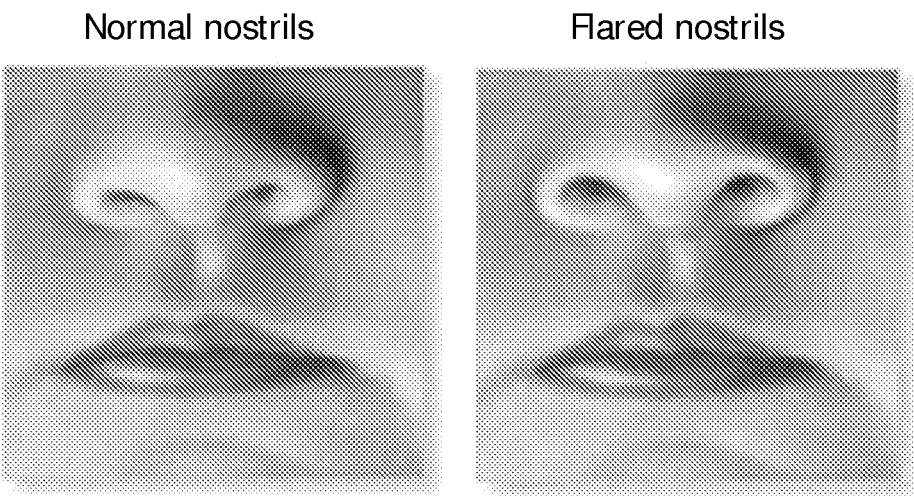
FIG. 1a and FIG. 1b shows normal nostrils, flared nostrils and intercostal and neck retractions of an exemplary subject under examination.
Figure 1B:
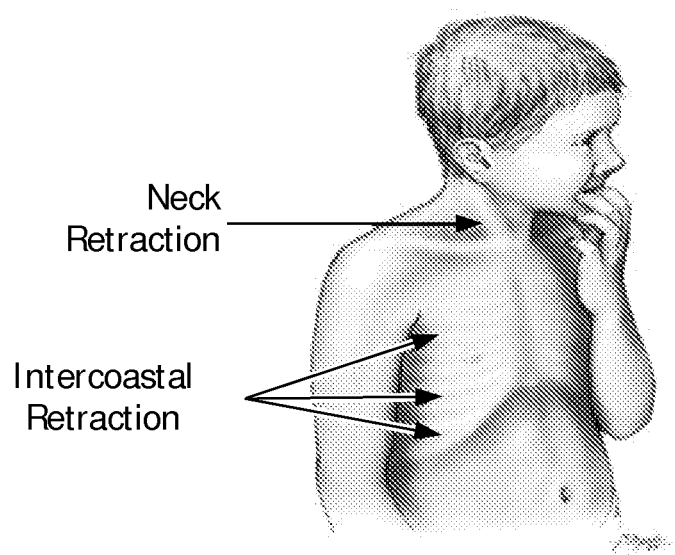

Referring now to FIG. 1a and FIG. 1b, the symptoms of asthma include i) nasal flaring wherein nostril size increases with breathing ii) neck retraction wherein neck area moves inward with breathing and iii) intercostal retraction wherein skin between or below the ribs move inward with breathing.

Figure 2A:
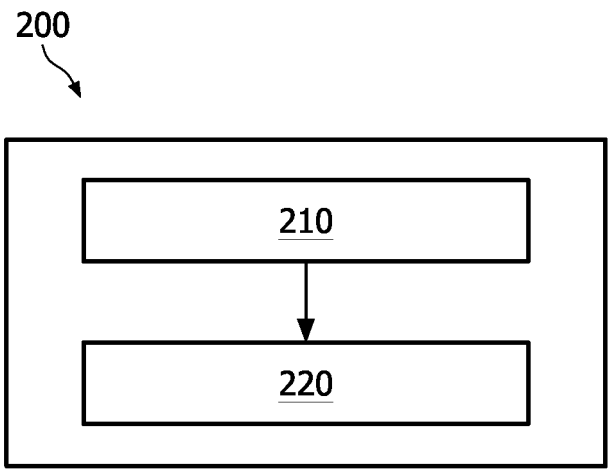
FIG. 2a shows an exemplary schematic block diagram of an apparatus for diagnosing asthma according to an embodiment of the present subject matter.

Referring now to FIG. 2a, the apparatus for diagnosing asthma 200 comprises
i) a data acquisition module 210
ii) an analysis module 220

The data acquisition module 210 can be configured to acquire at least one physical deformation feature of the subject under examination. The at least one physical deformation feature can be associated with at least one of the nasal flaring, the neck retraction and the intercostal retraction of the subject under examination.

The analysis module 220 can be configured to analyze the acquired at least one physical deformation feature associated with at least one of the nasal flaring, the neck retraction and the intercostal retraction of the subject under examination. Asthma can be diagnosed based on the analysis of least one physical deformation feature associated with at least one of the nasal flaring, the neck retraction and the intercostal retraction of the subject under examination.

The data acquisition module 210 can have at least one strain gauge. The at least one strain gauge can be configured to acquire at least one physical deformation feature associated with at least one of the nasal flaring, the neck retraction and the intercostal retraction of the subject under examination during at least one respiratory cycle. The at least one physical deformation feature can be acquired in the form of electrical variation associated with at least one of the nasal flaring, the neck retraction and the intercostal retraction of the subject under examination.

The at least one strain gauge can be attached to the nostrils or to the neck or to the intercostal region with the help of a suitable adhesive such as cyano-acrylate. The disclosed apparatus can facilitate the placement of the at least one strain gauge a) below or atop the tip of the nostril for acquiring at least one physical deformation feature associated with the nasal flaring b) in the area of the neck either bilaterally on right and left sides or unilaterally in between the lateral border of the sternocleidomastoid muscle and the upper border of the clavicle bone for acquiring at least one physical deformation feature associated with the neck retraction c) in one or more of the nine intercostal spaces in front of the chest either unilaterally or bilaterally for acquiring at least one physical deformation feature associated with the intercostal retraction The strain gauge can help in the measurement of physical deformations that evolve over time in the form of nasal flaring and suction of skin over the intercostal spaces and the neck region. As the nostrils or the neck region or the intercostal region deforms, the foil is also deformed, causing its electrical resistance to change. This resistance change can be measured using a Wheatstone bridge, which is related to the strain by a quantity known as gauge factor.

The idea disclosed is to measure the strain generated due to nasal flaring, chest and neck retraction and diagnose asthma based on the measurements.

Strain is a dimensionless unit, defined as a change in length per unit length. As an illustrative example, if a 1 meter long steel bar stretches to 1.000002 meter, the strain is defined as 2 micro strains. Strain gauges have a characteristic gauge factor, defined as the fractional change in resistance divided by the strain.

As an illustrative example, it could be that in the case of mild asthma, the nasal flaring causes 2 micro strain applied to a gauge with gauge factor of 2 and produces a fractional resistance change of $$(2 \times 2)10 = 4 \times 10^{-6} = 4 \text{ }\mu\text{Ohms}$$

This change would reflect in appropriate voltage dissipation at the circuit level given by $$V_0 = Vex(X/4)$$

Figure 2B:
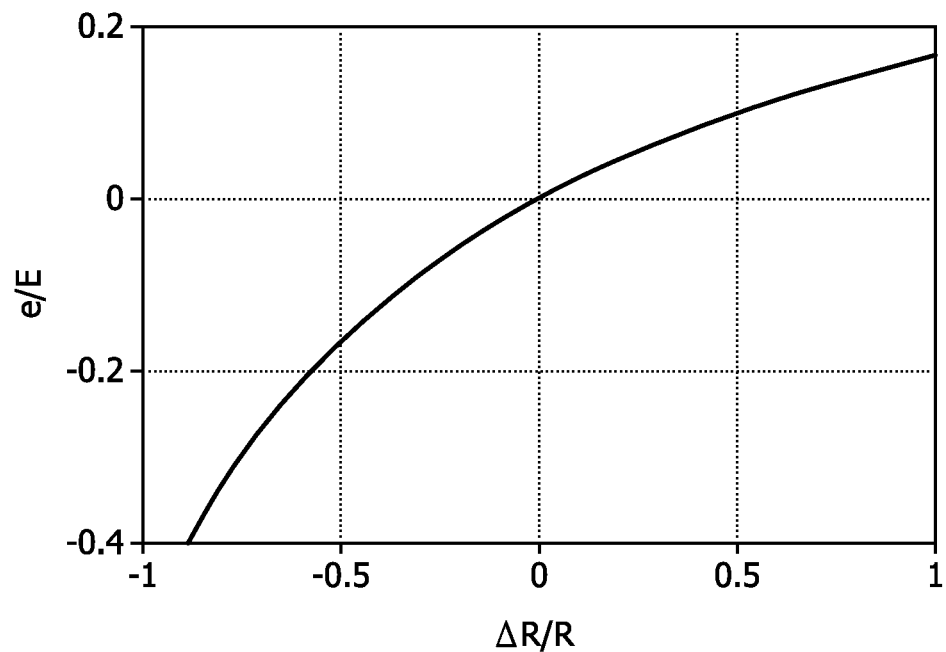
FIG. 2b schematically shows an exemplary variation in resistance v/s output voltage in an exemplary Wheatstone bridge.

Where
$V_0$=Bridge output voltage
Vex=excitation voltage applied to the bridge
X=relative change in resistance, BR/R FIG. 2b shows the resistance v/s output voltage variations in a typical wheat stone bridge. This output voltage from the wheat stone bridge is recorded by the disclosed apparatus 200. The variations in the output voltages can be recorded for 3 minutes and the corresponding data can be stored as an array of numbers. These numbers can be analyzed to extract features such as minimum voltage change and maximum voltage change in a window of approximately 3 minutes. These features can be compared with a database using Support Vector Machine to classify as mild asthma or normal. Similarly for medium asthma the nasal flaring can for e.g. reflect 5 micro strains and for severe asthma the nasal flaring can reflect for e.g. 8 micro strains. Chest and intercostal retractions can also be analyzed using similar techniques.

The at least one strain gauge can be a mercury-in-rubber strain gauge. This kind of strain gauge consists of a small amount of liquid mercury enclosed in a small rubber tube, which can be applied around the body part (nostrils, neck region and intercostal region). Physical deformation of the body part (nostrils, neck region and intercostal region) results in stretching of the tube, making it both longer and thinner, which increases electrical resistance.

The advantages of using strain gauge are:
a) there are no moving parts
b) relatively simple in construction
c) small in size
d) easy to dispose within the disclosed apparatus.

The strain gauge can acquire the physical deformations associated with at least one of the nasal flaring, the neck retraction and the intercostal retraction in the form of voltage/current variations. These variations are generally proportional to the amount of deformation that occurs during each respiratory cycle.

The strain gauges can be connected to data acquisition hardware which can record the voltage/current variations using analog components like resistors, capacitors and OP-AMPS. Analog to Digital Converters can be used to convert the analog signals of voltage/current waveforms into digital domain by properly sampling the signals. As an illustrative example, rate of respiration can be considered as input for choosing the right sampling frequency of Analog to Digital Converters. The rate of respiration in healthy subjects and diseased subjects generally vary from 12 to 25 respiratory cycles per minute. Hence, the sampling frequency can be chosen as >50.

Figure 3:
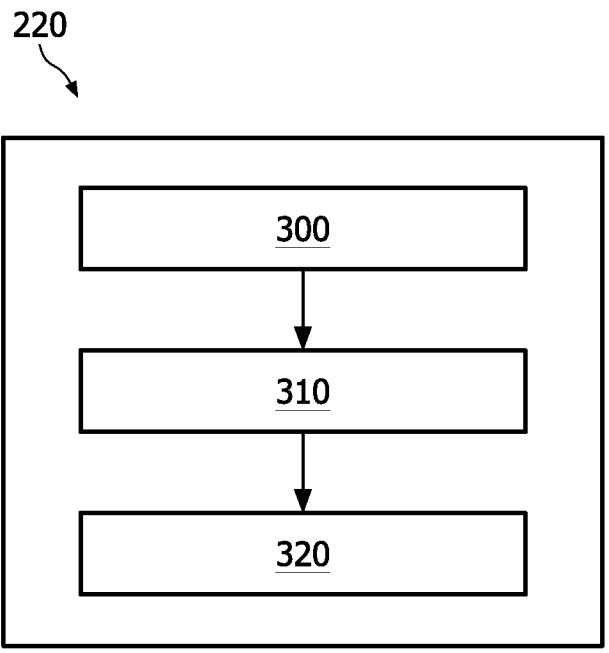
FIG. 3 shows an exemplary schematic block diagram of the analysis module according to an embodiment of the present subject matter.

Referring now to FIG. 3, the analysis module 220 for diagnosing asthma further comprises
a) a recording module 300
b) a feature extraction module 310
c) a storing module 320

The recording module 300 can be configured to digitally record for a pre-determined time period the acquired at least one physical deformation feature in the form of electrical variation associated with at least one of the nasal flaring, the neck retraction and the intercostal retraction of the subject under examination.

The feature extraction module 310 can be further configured to extract time domain features and/or frequency domain features from the digitally recorded at least one physical deformation feature in the form of electrical variation associated with at least one of the nasal flaring, the neck retraction and the intercostal retraction of the subject under examination.

The feature extraction module 310 can be configured to extract at least one of a) the respiratory cycles associated with at least one of the nasal flaring, the neck retraction and the intercostal retraction b) the average of the electrical variations over a pre-determined number of respiratory cycles associated with at least one of the nasal flaring, the neck retraction and the intercostal retraction c) the frequency bands present in the respiratory cycles associated with at least one of the nasal flaring, the neck retraction and the intercostal retraction d) the minimum frequency band and the maximum frequency band present in the respiratory cycles associated with at least one of the nasal flaring, the neck retraction and the intercostal retraction.

The pattern of breathing, which includes the respiratory rate, rhythm and effort, can provide a useful practical tool for assessing the respiratory system. The presence of dis-coordinated breathing (lack of coordination between thoracic and diaphragmatic muscles of respiration) is also a poor sign. In its extreme form, there is failure of synchronization and the chest moves inward during inspiration.

Increased respiratory effort and work of breathing may be evaluated by assessment of accessory muscle use, sub costal and inter-costal retractions, nasal flaring, and the rate and depth of respiratory effort. Children in moderate to severe respiratory distress will present in the initial states with marked accessory muscle activity as well as sub coastal and intercostal retractions. Nasal flaring may indicate mild asthma, but use of sternocleidomastoid and other accessory muscles signifies increasing respiratory effort.

Asthma can be better diagnosed with the help of the extracted features. The extracted features can also help in carrying out a comparative analysis with other available baseline features and can further improve the diagnosis of asthma.

The storing module 320 can be configured to store the extracted time domain feature and/or frequency domain feature electrical variation associated with at least one of the nasal flaring, the neck retraction and the intercostal retraction of the subject under examination.

The parents can use the disclosed apparatus 200 for recording and storing the extracted physical deformation features associated with the neck retraction, the nasal flaring and the intercostal retraction of their child. During the scheduled visit to the hospital, the doctor can analyze and interpret the stored recordings and diagnose the condition of the child for asthma.

Recording and storing the extracted features can a) help the doctor to flawlessly formulate the clinical profile of the child (patient or subject) and prescribe suitable treatment b) be useful for effective monitoring of the subjects already under treatment especially small children known to have asthma to have precise understanding of symptom evolution and remission c) act as a history for tracking the trend of asthma evolution d) be clinically useful for especially young children, infants and elderly patients, patients with mental retardation or other behavioral disorders since these are the group of subjects (patients or children) who may not be able to conceive and convey their breathing problems accurately to the doctor.

Generally, by the time the subject (patient or child) reaches the doctor the disease symptoms and signs would have subsided at least partially. This can give an incomplete clinical picture to the doctor and can result in incorrect diagnosis. The stored extracted physical deformation features associated with at least one of the nasal flaring, the neck retraction and the intercostal retraction can overcome the risk of arriving at incorrect diagnosis.

Figure 4A:
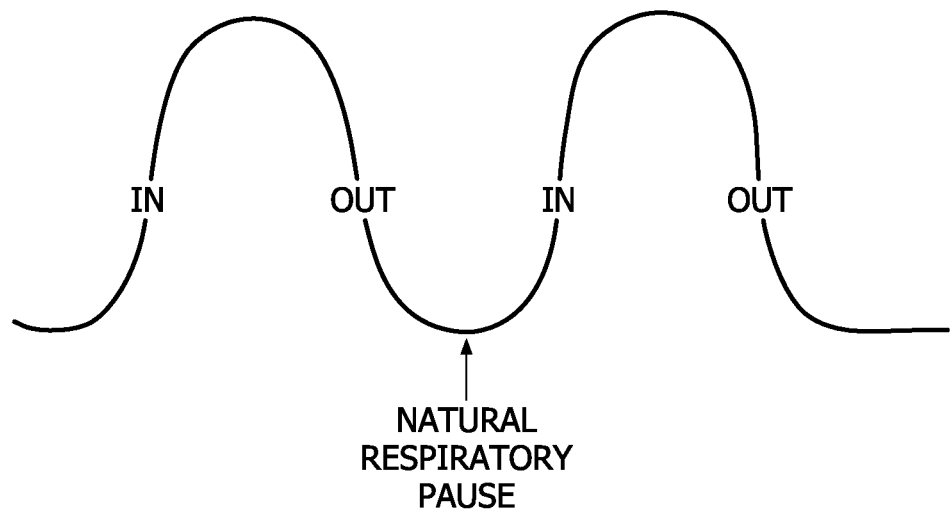
FIG. 4a-FIG. 4c schematically shows exemplary waveforms.

The pattern of a normal respiratory cycle is shown in FIG. 4a. The respiratory cycle refers to the cyclical and rhythmic process of taking air into the lungs by a process called as inspiration and expelling out the air from the lungs by a process called as expiration with a pause in between inspiration and expiration. The process of respiration is mediated or controlled by the respiratory center in the brain stem consisting of inspiratory and expiratory centers. Normal respiratory rate generally varies between 14-20 times per minute under various physiological conditions and is usually less than 25 times/minute.

Figure 4B:
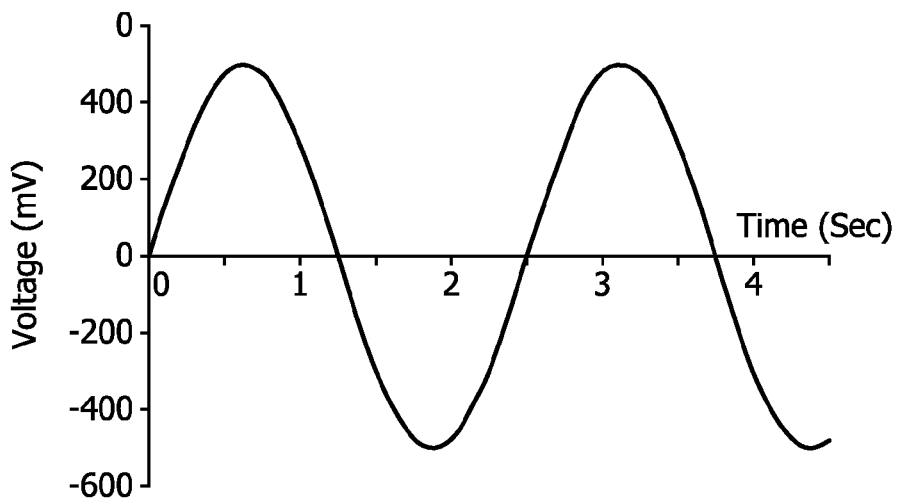

FIG. 4b shows an exemplary electrical waveform generated by the strain gauge associated with the normal respiratory cycle in a healthy subject. As can be seen from the graph, the voltage generation by the strain gauges placed at the nostrils or the neck or the intercostal region is generally in the range of 400-500 mV in a healthy subject. The frequency band of the electrical waveform of the healthy subject is generally around 0.5 Hz.

Figure 4C:
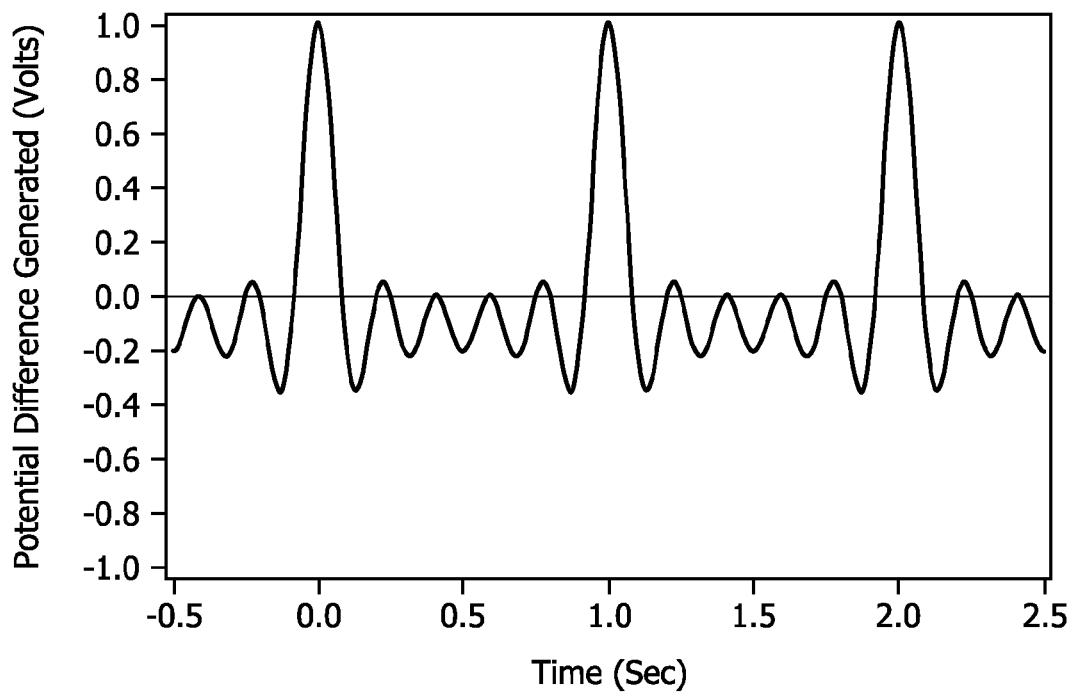

FIG. 4c shows an exemplary electrical waveform associated with the intercostal retraction of a severe asthmatic subject. The electrical waveform is suggestive of generation of progressively higher voltages and higher variations (zero crossings) in the time domain, leading to higher frequency bands in frequency domain. It is possible to divide the subjects into groups having mild asthma, moderate asthma and severe asthma based on the pattern of the variations in time domain, amplitude of the voltages and frequency bands. As an illustrative example, it is possible to deduce from FIG. 4c that the value of the potential difference generated through the strain gauge in a subject with mild asthma, moderate asthma and severe asthma is around 600, 800 and 1000 mV respectively. In the frequency domain the frequency bands of the electrical waveform for mild asthma, moderate asthma and severe asthma are around 3 Hz, 6 Hz and 10 Hz respectively.

Figure 5:
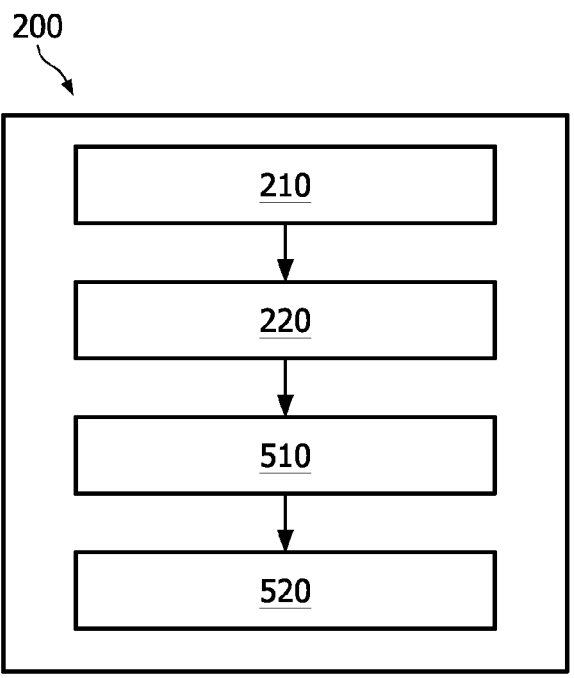
FIG. 5 shows an exemplary schematic block diagram of an apparatus for diagnosing asthma according to a still further embodiment of the present subject matter.

Referring now to FIG. 5, the apparatus 200 for diagnosing asthma further comprises an input module 510 configured to receive input, the input being at least one of gender, age, height, weight and ethnicity of the subject under examination a pre-classified calibrated database 520 having data associated with non-asthmatic subjects and asthmatic subjects, the data being at least one of i) gender ii) age iii) height iv) weight v) ethnicity vi) time domain and/or frequency domain features extracted using the acquired physical deformations acquired in the form of electrical variation associated with at least one of the nasal flaring, the neck retraction and the intercostal retraction vii) condition of the subject: non-asthmatic, onset of asthma, mild asthma, acute asthma The input module helps to collect data of the subject under examination. This input data can help in grouping the subjects and identifying symptoms related to asthma within the groups. Further, the collected data can help in carrying out a comparative study with the extracted physical deformation features with similar subjects. This can further improve the diagnosis of asthma. Further, in developing countries, where economies do not permit every family to own the disclosed apparatus, families can own a shared apparatus which can be used on a need basis. In such cases, the input module can be of help to identify the subject under examination and the stored physical deformation features associated with at least one of the nasal flaring, the neck retraction and the intercostal retraction of the subject under examination.

The pre-classified calibrated database can act as a baseline. It can help in classifying the physical deformations of the subject under examination associated with at least one of the nasal flaring, the intercostal retraction and the neck retraction into different grades of asthma. The different grades of asthma can be onset of asthma, mild asthma and severe asthma.

The pre-classified calibrated database can be periodically calibrated. This can be done by testing the disclosed apparatus across sufficient number of subjects based on age, height, weight, gender and ethnicity. The physical deformations associated with at least one of the nasal flaring, the neck retraction, and the intercostal retraction can be acquired. The time domain features and/or frequency domain features can be extracted, labeled as non-asthmatic/asthmatic subject and stored in the database. The pre-classified calibrated database can be a useful tool for diagnosing asthma.

Figure 6:
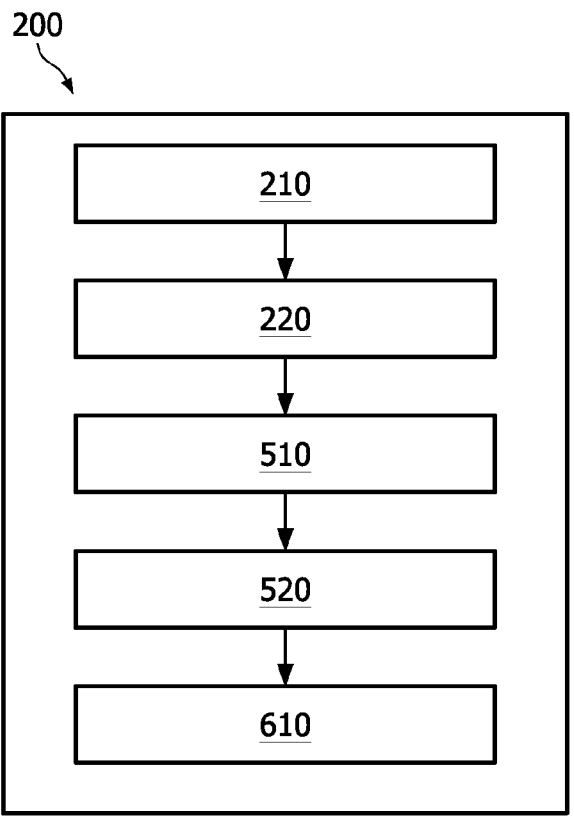
FIG. 6 shows an exemplary schematic block diagram of the analysis module according to an embodiment of the present subject matter.

Referring now to FIG. 6, the analysis module 220 further comprises a logic module 610 configured to compare the extracted time domain and/or frequency domain physical deformations associated with at least one of the nasal flaring, the neck retraction and the intercostal retraction of the subject under examination with the data available in the pre-classified calibrated database and diagnose the asthma condition of the subject under examination and store the diagnosis related information.

Known pattern matching algorithms can be used to compare the extracted time domain and/or frequency physical deformations associated with at least one of the nasal flaring, the neck retraction and the intercostal retraction with the extracted physical deformation time domain and/or frequency domain features available in the pre-classified calibrated database. The condition of the subject under examination can be obtained based on the classification results. It is also possible to obtain the grade of the asthma e.g. onset of asthma, mild asthma or severe asthma.

In some embodiments, a Support Vector Machine (SVM) can be used for classification. As an illustrative example, the SVM can view input data as two sets of vectors; one set corresponding to the actual features extracted using the strain gauges and the other set corresponding to the data available in the pre-classified calibrated database of asthmatic and non-asthmatic subjects. The SVM can construct a separating hyper plane in an n-dimensional space, the hyper plane being the one which maximizes the margin between the two data sets. To calculate the margin, two parallel hyper planes can be constructed, one on each side of the separating hyper plane, which is "pushed up against" the two data sets. Intuitively, a good separation can be achieved by the hyper plane that has the largest distance to the neighboring data points of both classes, since in general the larger the margin the better the generalization error of the classifier.

Figure 7:
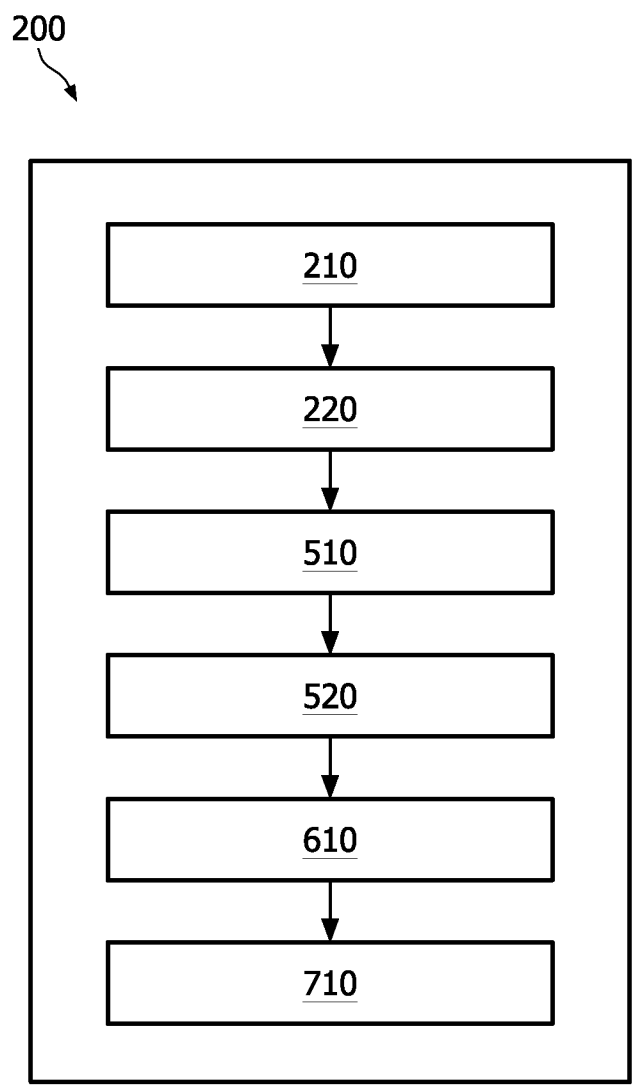
FIG. 7 shows an exemplary schematic block diagram of an apparatus for diagnosing asthma according to a still further embodiment of the present subject matter.

Referring now to FIG. 7, the apparatus for diagnosing asthma 200 further comprises a notification module 710 configured to notify i) whether at least one of the nasal flaring, the neck retraction and the intercostal retraction is detected ii) the need for emergency consultation if the diagnosed asthma is above a pre-determined threshold iii) that there is no need for emergency consultation if the diagnosed asthma is below a pre-determined threshold. The notification module 710 can be at least one of a visual display unit, an audio unit or a color light generation unit.

This embodiment has the following advantages i) it can avoid panic and discomfort of having severe asthmatic attack ii) minimize the need for emergency visits or hospitalizations iii) can bring down the cost of treatment by avoiding unnecessary consultation iv) can prevent recurrent exacerbations of asthma.

The disclosed apparatus can notify the results in the form of visual display and indicate the severity of asthma to the subject under examination. Alternately, an alarm beep could guide both the adult patients and the anxious parents of the sick children to seek medical consultation immediately in case of severe asthma.

The subjective evaluation of nasal flaring, intercostal retraction and neck retraction may not be reliable. There could be some variations in inter-observer (i.e. between different doctors) agreement on intercostal retractions and interpretation. To overcome these limitations, the nasal flaring, the neck retractions and the intercostal retractions are recorded and the extracted features are stored in digital form. The stored features can be visualized by the doctor. This can further aid in improving the diagnosis of asthma by providing objective information about the symptoms.

The disclosed apparatus can also give information directly as to whether the nasal flaring, the neck retraction and the intercostal retraction are present in the form of colored lights. Further, the waveforms representing the physical deformations associated with at least one of the nasal flaring, the neck retraction and the intercostal retraction can be displayed. This can form reliable input to the doctor to objectively evaluate the symptoms thereby easing the normal work flow of asthma diagnosis, assessment of asthma activity and response to treatment. This can further improve the diagnosis of asthma.

Figure 8:
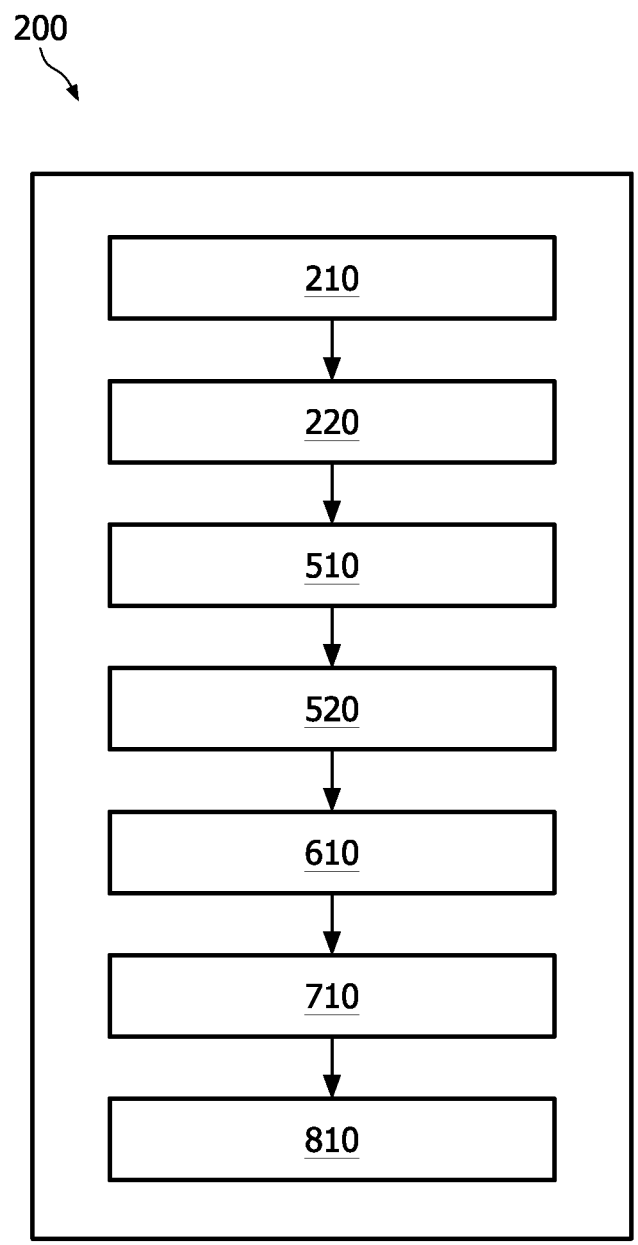
FIG. 8 shows an exemplary schematic block diagram of an apparatus for diagnosing asthma according to a still further embodiment of the present subject matter.

Referring now to FIG. 8, the apparatus for diagnosing asthma 200 further comprises an evaluation module 810 configured to evaluate the progress of the therapy or remission based on i) the currently acquired at least one physical deformation feature associated with at least one of the nasal flaring, the neck retraction and the intercostal retraction of the subject under examination ii) the previously stored physical deformation feature associated with at least one of the nasal flaring, the neck retraction and the intercostal retraction of the subject under examination. The disclosed apparatus can be used to assess the evolution of asthma and the response to treatment as it provides objective measurements of asthma severity in the form of reduction/increase in the nasal flaring, the chest retraction and the intercostal retraction during the period of remission.

Figure 9:
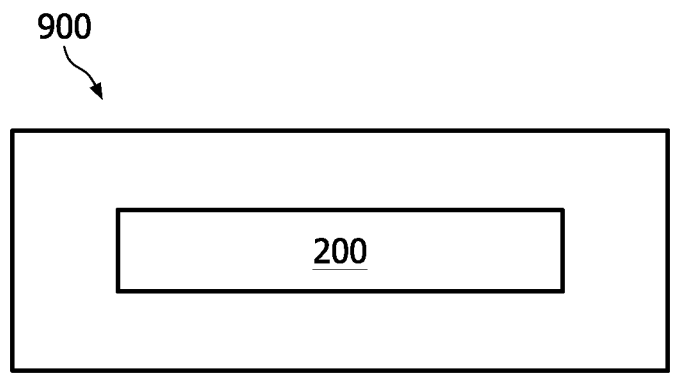
FIG. 9 schematically shows an exemplary wheeze monitoring device.

The disclosed apparatus can be built as a standalone system or as an add-on to the existing devices for monitoring the asthma symptoms. Referring now to FIG. 9, the disclosed apparatus 200 for diagnosing asthma can be used as an add-on apparatus for a wheeze monitoring device. The data from the strain gauges can be fed wirelessly or through wired connection to the wheeze monitoring device. The wheeze monitoring device can subsequently use this data as an additional input along with the wheezes to estimate the severity of asthma. This can further improve the diagnosis of asthma.

Figure 10:
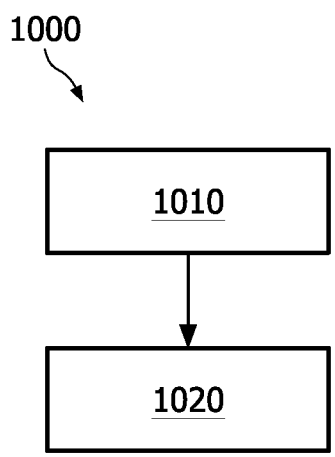
FIG. 10 schematically shows an exemplary flow chart illustrating the method of diagnosing asthma according to an embodiment of the present subject matter.

Referring now to FIG. 10, the method for diagnosing asthma 1000 comprises a step 1010 of acquiring at least one physical deformation feature associated with at least one of the nasal flaring, the neck retraction and the intercostal retraction and a step 1020 of analyzing the acquired at least one physical deformation feature associated with at least one of the nasal flaring, the neck retraction and the intercostal retraction and diagnosing asthma based on the analyzed at least one physical deformation feature associated with at least one of the nasal flaring, the neck retraction and the intercostal retraction.

The present subject matter discloses the use of strain gauges for measuring mechanical changes that evolve over time in diseases of airway obstruction in the form of nasal flaring and suction of skin over intercostal spaces and neck region. Further, these mechanical changes are calibrated to find the severity of the diseased condition.

In summary, an apparatus for diagnosing asthma is disclosed. The apparatus comprises a data acquisition module configured to acquire at least one physical deformation feature associated with at least one of nasal flaring, neck retraction and intercostal retraction of a subject under examination and an analysis module configured to analyze the acquired at least one physical deformation feature associated with at least one of the nasal flaring, the neck retraction and the intercostal retraction of the subject under examination and diagnose the asthma based on the analyzed at least one physical deformation feature associated with at least one of the nasal flaring, the neck retraction and the intercostal retraction of the subject under examination.

The disclosed apparatus can be used for monitoring asthma at home, at hospital or in ambulatory patients. The disclosed apparatus can also give indication of development of other airway obstruction related diseases such as Transient Tachypnea of the Newborn, Choanal Atresia, Persistent tachypnea in infants, Bronchiolitis, Croup, Acute epiglottitis wherein chest and nest retractions and nasal flaring could be one of the clinical features.

While the subject matter has been illustrated in detail in the drawings and foregoing description, such illustration and description are to be considered illustrative or exemplary and not restrictive; the subject matter is not limited to the disclosed embodiments. Other variations to the disclosed embodiments can be understood and effected by those skilled in the art of practicing the claimed subject matter, from a study of the drawings, the disclosure and the appended claims. Use of the verb "comprise" and its conjugates does not exclude the presence of elements other than those stated in a claim or in the description. Use of the indefinite article "a" or "an" preceding an element or step does not exclude the presence of a plurality of such elements or steps. A single unit may fulfill the functions of several items recited in the claims. The mere fact that certain measures are recited in mutually different dependent claims does not indicate that a combination of these measures cannot be used to advantage. The figures and description are to be regarded as illustrative only and do not limit the subject matter. Any reference sign in the claims should not be construed as limiting the scope.

The invention claimed is:

1. An apparatus for diagnosing asthma, the apparatus comprising;
   a data acquisition module configured to acquire measurements of nasal flaring and neck refraction of a subject under examination wherein the data acquisition module comprises
   a first strain gauge adapted to be placed on a nostril of the subject and configured to acquire measurements of nasal flaring of the subject during at least one respiratory cycle; and
   a second strain gauge adapted to be placed on a neck of the subject and configured to acquire measurements of neck retraction of the subject under examination during at least one respiratory cycle; wherein the physical deformation features are measured in a form of electrical variation associated with nasal flaring and neck retraction of the subject under examination; and
   an analysis module configured to analyze the acquired measurements of nasal flaring and neck retraction of the subject under examination and diagnose the asthma based on the analyzed measurements of nasal flaring and neck retraction of the subject under examination.

2. The apparatus as claimed in claim 1, wherein the at least one strain gauge is a mercury-in-rubber strain gauge.

3. The apparatus as claimed in claim 2, wherein the analysis module further comprises
   a recording module configured to digitally record for a pre-determined time period the acquired at least one physical deformation feature in the form of electrical variation associated with nasal flaring, neck retraction and intercostal refraction of the subject under examination;
   a feature extraction module configured to extract time domain feature and/or frequency domain feature from the digitally recorded at least one physical deformation feature in the form of electrical variation associated with the nasal flaring, the neck retraction and the intercostal retraction of the subject under examination; and
   a storing module configured to store the extracted time domain feature and/or frequency domain feature electrical variation associated with the nasal flaring, the neck retraction and the intercostal retraction of the subject under examination.

4. The apparatus as claimed in claim 3, wherein the feature extraction module is configured to extract at least one of
   a) respiratory cycles associated with the nasal flaring, the neck retraction and the intercostal retraction
   b) an average of the electrical variations over a pre-determined number of respiratory cycles associated with the nasal flaring, the neck retraction and the intercostal retraction
   c) frequency bands present in the respiratory cycles associated with nasal flaring, the neck retraction and the intercostal retraction
   d) a minimum frequency band and a maximum frequency band present in the respiratory cycles associated with the nasal flaring, the neck retraction and the intercostal retraction.

5. The apparatus as claimed in claim 3, wherein the analysis module further comprises
   an input module configured to receive input, the input being at least one of gender, age, height, weight and ethnicity of the subject under examination; and
   a pre-classified calibrated database having physical deformation data associated with non-asthmatic subjects and asthmatic subjects, the physical deformation data including time domain and/or frequency domain features and at least one additional feature of
a) gender
b) age
c) height
d) weight
e) ethnicity
f) wherein the time domain and/or frequency domain features are extracted using the acquired physical deformations in the form of electrical variation associated with the nasal flaring, the neck refraction and the intercostal retraction
g) condition of the subject: non-asthmatic, onset of asthma, mild asthma, acute asthma.

6. The apparatus as claimed in claim 5, wherein the analysis module further comprises a logic module configured to compare physical deformations of the extracted time domain and/or frequency domain associated with the nasal flaring, the neck retraction and the intercostal retraction of the subject under examination with the data available in the pre-classified calibrated database and diagnose the asthma condition of the subject under examination and store the diagnosis related information.

7. The apparatus as claimed in claim 1, further comprising a notification module, the notification module being at least one of a visual display unit, an audio unit or a colored light generation unit, the notification module configured to notify when one or more of the following conditions are met: i) whether the nasal flaring, the neck retraction and an intercostal retraction is detected ii) the need for emergency consultation if the diagnosed asthma is above a pre-determined threshold iii) that there is no need for emergency consultation if the diagnosed asthma is below a pre-determined threshold.

8. The apparatus as claimed in claim 1, further comprising an evaluation module configured to evaluate the progress of therapy or remission based on the evaluation of one or more of the following features: i) the acquired measurements of nasal flaring and neck retraction and/or an inter-coastal refraction of the subject under examination ii) a previously stored physical deformation feature associated with the nasal flaring, the neck retraction and/or the intercostal retraction of the subject under examination.

9. The apparatus as claimed in claim 1, further comprising a wheeze monitoring device, wherein the analysis module diagnoses the asthma based on an output from the wheeze monitoring device.

10. A method for diagnosing asthma, the method being implemented in a computer system including one or more physical processors storage media storing machine-readable instructions, and two or more strain gauges, the method comprising
acquiring data from physical deformation features associated with nasal flaring and neck retraction of a subject, wherein the acquiring data comprises;
placing a first strain gauge on a nostril of the subject, wherein the first strain gauge is configured to acquire measurements of nasal flaring of the subject during at least one respiratory cycle; and
placing a second strain gauge on a neck of the subject, wherein the second strain gauge is configured to acquire measurements of neck retraction of the subject during at least one respiratory cycle;
wherein the physical deformation features are measured in a form of electrical variation associated with nasal flaring and neck retraction of the subject under examination;
analyzing the acquired data for physical deformation features associated with each of the nasal flaring and the neck retraction; and
comparing the acquired data with stored diagnostic data patterns indicative of diagnosing asthma based on the analyzed physical deformation features associated with nasal flaring and neck retraction.

\* \* \* \* \*